US00PP16435P2

(12) United States Plant Patent
Laviana

(10) Patent No.: US PP16,435 P2
(45) Date of Patent: Apr. 11, 2006

(54) ***HOSTA* PLANT NAMED 'TIME TUNNEL'**

(50) Latin Name: *Hosta sieboldiana*
Varietal Denomination: Time Tunnel

(75) Inventor: Marc R. Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 116 days.

(21) Appl. No.: 11/007,411

(22) Filed: Dec. 8, 2004

(51) Int. Cl.
*A01H 5/00* (2006.01)

(52) U.S. Cl. ..... Plt./353
(58) Field of Classification Search ..... Plt./353
See application file for complete search history.

*Primary Examiner*—Anne Marie Grunberg
(74) *Attorney, Agent, or Firm*—Penny J. Aguirre

(57) ABSTRACT

A new cultivar of *Hosta sieboldiana*, 'Time Tunnel', characterized by its variegated foliage of green centers and wide margins that emerge chartreuse, change to a bright gold, and mature to a creamy gold color. The margins of the foliage of 'Time Tunnel' are much wider than its parent plant, 'Frances Williams', comprising about 50% of the leaf area.

2 Drawing Sheets

Botanical classification: *Hosta sieboldiana.*
Cultivar designation: 'Time Tunnel'.

BACKGROUND OF THE INVENTION

The present invention *Hosta* 'Time Tunnel', relates to a new and distinct cultivar of *Hosta sieboldiana* and will hereinafter be referred to as 'Time Tunnel'.

The inventor discovered the new cultivar, 'Time Tunnel' as a whole plant mutation of *Hosta sieboldiana* 'Frances Williams' (unpatented) at his nursery in Kensington, Conn. in April of 2000. 'Time Tunnel' was discovered in a plug tray of 'Frances Williams' that originated as rooted transplants produced by micropropagation. 'Time Tunnel' was selected as unique for its variegated leaf pattern of wide golden colored margins surrounding green centers. 'Frances Williams' has foliage with a similar variegation pattern, however the margins of 'Time Tunnel' are significantly wider.

Asexual reproduction of the new cultivar was first accomplished by in vitro propagation in Kensington, Conn. in the spring of 2002. Asexual reproduction of the new cultivar by division and tissue culture has shown that the unique features of 'Time Tunnel' are stable and reproduced true to type in successive generations.

SUMMARY OF THE INVENTION

The following traits have been repeatedly observed and represent the characteristics of the new cultivar. These attributes in combination distinguish 'Time Tunnel' as a new and unique cultivar of *Hosta.*

1. 'Time Tunnel' has variegated foliage with green centers and wide margins that emerge chartreuse, change to a bright gold, and mature to a creamy gold color.
2. The margins of the foliage of 'Time Tunnel' are about twice the width of the parent plant, 'Frances Williams'. The wide margins of 'Time Tunnel' comprise about 50% of the leaf area and are retained throughout the growing season.
3. 'Time Tunnel' exhibits white flowers in mid summer, similar to 'Frances Williams'.

BRIEF DESCRIPTION OF THE DRAWINGS

The accompanying colored photographs were taken in late summer and illustrate the overall appearance and distinct characteristics of the new *Hosta*. The plants in the photographs are three year-old plants of 'Time Tunnel' as grown outdoors in Kensington, Conn. in medium shade.

Figure 1:
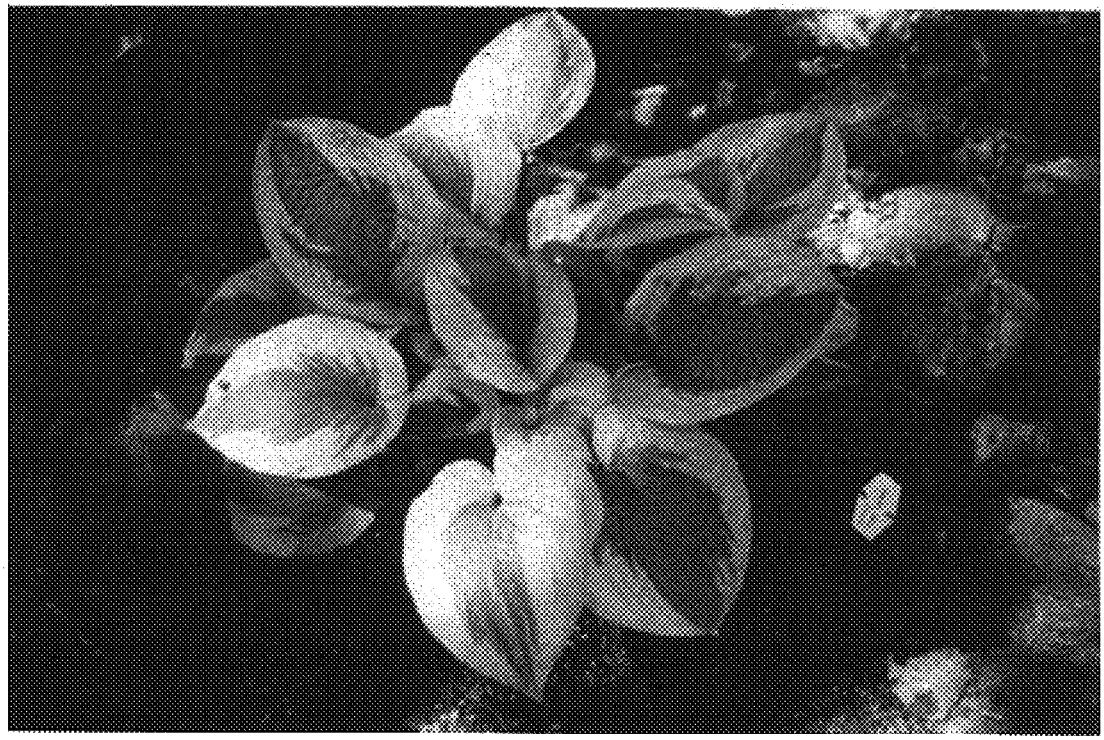
FIG. 1 provides an overall view of new cultivar.
Figure 2:
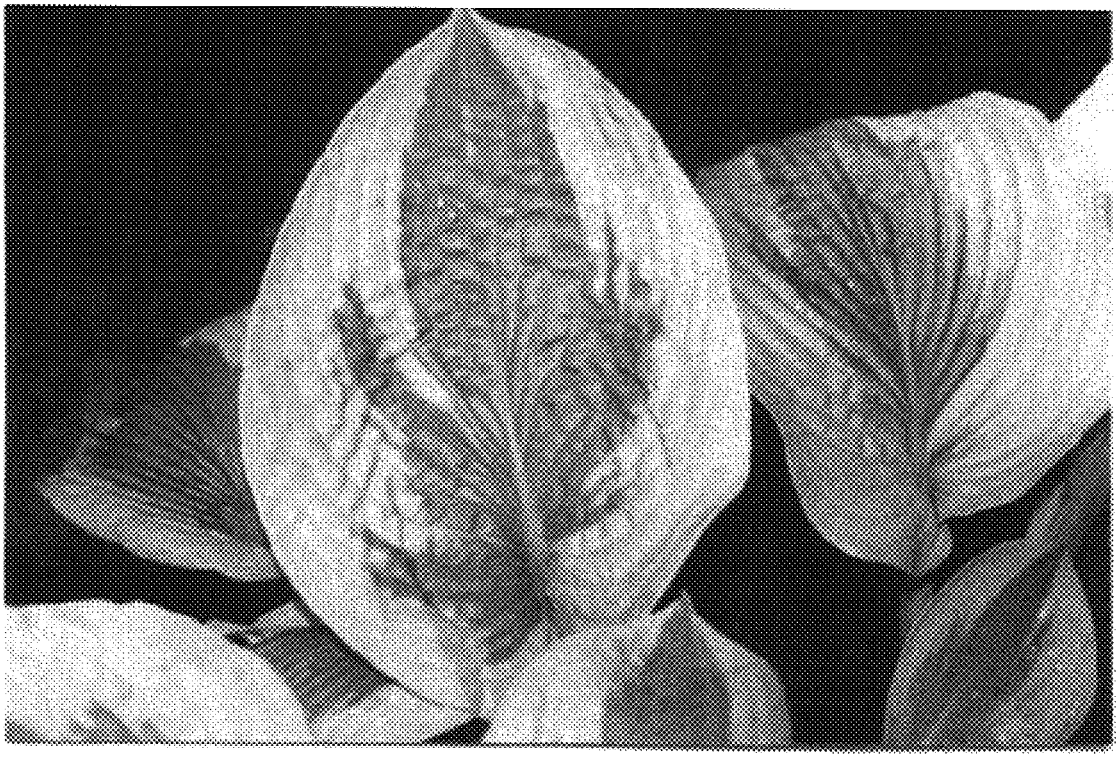
FIG. 2 is of a close-up view of the foliage of 'Time Tunnel'.

The colors in the photographs are as close as possible with the photographic and printing technology utilized. The color values cited in the detailed botanical description accurately describe the colors of the new *Hosta.*

DETAILED BOTANICAL DESCRIPTION OF THE PLANT

The following is a detailed description of 3 year-old plants of the new cultivar as grown outdoors in Kensington, Conn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Time Tunnel' is a cultivar of *Hosta sieboldiana.*

Parentage: Naturally occurring whole plant mutation of *Hosta sieboldiana* 'Frances Williams' (syn. *Hosta* 'Frances Williams').

General description:

*Blooming period.*—From mid June to mid July.

*Plant habit.*—Herbaceous perennial, clump-forming, open-mounded foliage of large size.

*Height and spread.*—Foliage reaches up to about 53 cm (22 inches) in height and up to about 91 cm (36 inches) in width.

*Hardiness.*—Zone 3–8.

*Culture*.—Full shade to part shade in moist, organic rich soils.

*Diseases and pests*.—No susceptibility or resistance to diseases or pests has been observed for 'Time Tunnel'. Thick substance of leaves may confer slug resistance.

*Root description*.—Freely branched, fleshy.

*Propagation*.—In vitro propagation is the preferred method utilizing typical methods for *Hosta*, division are also possible.

*Root development*.—Rooted transplants from tissue culture fully develop in a 32-cell liner in about 6 to 8 weeks in a greenhouse with average temperatures of about 70° F.

*Growth rate*.—Moderately vigorous.

Foliage description:

*Leaf shape*.—Broadly cordate to broadly ovate.

*Leaf division*.—Simple.

*Leaf base*.—Cordate.

*Leaf apex*.—Cuspidate.

*Leaf venation*.—About 16 pairs of veins, camptodrome pattern, venation is noticeable due to rugose nature of leaves, sunken on upper surface and protruding on lower surface, vein color on both surfaces matches leaf color.

*Leaf margins*.—Entire with irregular undulation.

*Leaf attachment*.—Petiolate.

*Leaf arrangement*.—Basal, radiate spirally from base.

*Leaf orientation*.—Held horizontal to slightly arching downward to slightly cupped upward on mature, heavily rugose leaves, petioles held upright at an angle about 80 to 90°.

*Leaf surface*.—Upper and lower: glaucous with lower surface more glaucous, mature leaves are rugose.

*Leaf color*.—Young leaves (upper surface): centers N138A to N138B, margins 144A to 144B, intermediate area 139C. Young leaves (lower surface): centers 189A, margins between 144B and 139C, intermediate area is not distinct. Maturing leaves (upper surface): centers 139A and 139B, margins N144A to N144B, intermediate area 139C. Maturing leaves (lower surface): centers 138B, margins N144A and 139B, intermediate area is not distinct. Mature leaves (upper surface): centers 139A and 139B, margins 160A to 160C to 155D, intermediate area 139C to 139D. Mature leaves (lower surface): centers 138B, margins 160B to 160C to 155D, intermediate area not distinct.

*Leaf variegation pattern*.—For mature leaves, on average the margin comprises about 50% of the leaf area. In comparison, the margin of the parent plant, 'Frances Williams', comprises about 20% of the leaf area.

*Leaf size*.—Up to about 25 cm (10 inches) in length, up to about 20 cm (8 inches) in width. Measurements on a three year-old plant, leaf size may become larger after more years of maturity.

*Leaf quantity*.—Average 5 per shoot (eye).

*Petiole size*.—Average of 12 cm in length, up to about 1.2 cm in width.

*Petiole color*.—144A on inner surface, 144B on outer surface.

*Petiole shape*.—Sulcate.

Flower scape description:

*Scape shape*.—Round, solid.

*Scape number*.—One per mature eye under normal growing conditions.

*Scape posture*.—Straight, strong, held upright at about 80 to 90° from horizontal.

*Scape size*.—About 53 to 60 cm in length, about 5 mm in width and tapering to 1 mm at apex.

*Scape color*.—144A.

*Scape surface*.—Glaucous.

*Leaf bracts*.—1 per scape, 144B in color, ovate in shape, average of 5 cm in length and 3.5 cm in width.

*Flower bracts*.—1 per flower, broadly elliptic, 85D in color, about 2 cm in length and about 1.25 cm in width.

Flower description:

*Inflorescence type*.—Terminal racemes on elongated flower scapes.

*Lastingness of inflorescence*.—About 3 to 4 weeks from first opening bloom to fading of last opening bloom, individual blooms last about one week.

*Flower shape*.—Bell-shaped (campanulate-tubular).

*Flower arrangement*.—Alternate on raceme.

*Flower fragrance*.—Slight sweet fragrance.

*Flower number*.—About 28 per scape.

*Flower bud shape*.—Obovate.

*Flower bud size*.—Up to about 3.5 cm in length and about 1.2 cm in width.

*Flower bud color*.—85D.

*Flower size*.—Fully open: About 4.7 cm in length and up to about 2.7 cm in width.

*Flower color*.—N155B, effective color is white with a slight blush of lavender.

*Flower aspect*.—Outward and slightly pendulous.

*Pedicels*.—About 2 mm in diameter, 1.7 cm in length, 138B in color, texture is glabrous.

*Perianth features*.—Comprised of 6 Tepals, 3 interior and 3 exterior, overlapping in expanded region and fused in tube region.

*Tepal characteristics*.—Effectively white in color N155A suffused in lavender 85D on center of each tepal (upper and lower surfaces), about 4.6 cm in length, about 1.2 cm in width, acute apex, entire margins, glabrous texture.

Reproductive organs:

*Gynoecium*.—1 pistil, style; about 4.7 mm in length width and 1 mm in diameter, 155C in color, stigma; 1-lobed and 155C in color, ovary; compound, 5 mm in height, 4 mm in diameter, composed of 3 locules.

*Androecium*.—6 stamens, 1 mm in width, 3.5 cm in length, filaments; 155C in color, anthers; oblong in shape, 4 mm in length, 5 mm in width, attachment is dorsifixed, 86C in color, pollen; low in abundance, 21A in color.

*Seed*.—Capsule; 2.7 cm in length, 7 mm in diameter, 138B in color, texture is glabrous seed; flattened oval in shape, 8 mm in length, 4 mm in width, average of 12 per capsule, 202A in color.

I claim:

1. A new and distinct cultivar of *Hosta* plant named 'Time Tunnel' as herein illustrated and described.

* * * * *